US010555773B2

(12) United States Patent
Higaki et al.

(10) Patent No.: US 10,555,773 B2
(45) Date of Patent: Feb. 11, 2020

(54) SIMULATOR, INJECTION DEVICE OR IMAGING SYSTEM PROVIDED WITH SIMULATOR, AND SIMULATION PROGRAM

(71) Applicants: HIROSHIMA UNIVERSITY, Hiroshima (JP); NEMOTO KYORINDO CO., LTD., Tokyo (JP)

(72) Inventors: Toru Higaki, Hiroshima (JP); Kazuo Awai, Hiroshima (JP); Yuko Nakamura, Hiroshima (JP); Kazumasa Masuda, Tokyo (JP); Koji Yuba, Tokyo (JP); Shigeru Nemoto, Tokyo (JP)

(73) Assignees: HIROSHIMA UNIVERSITY, Hiroshima (JP); NEMOTO KYORINDO CO., LTD., Tokyo (JP)

( * ) Notice: Subject to any disclaimer, the term of this patent is extended or adjusted under 35 U.S.C. 154(b) by 105 days.

(21) Appl. No.: 15/529,373

(22) PCT Filed: Nov. 26, 2015

(86) PCT No.: PCT/JP2015/005861
§ 371 (c)(1),
(2) Date: May 24, 2017

(87) PCT Pub. No.: WO2016/084373
PCT Pub. Date: Jun. 2, 2016

(65) Prior Publication Data
US 2017/0281278 A1 Oct. 5, 2017

(30) Foreign Application Priority Data

Nov. 27, 2014 (JP) .................................. 2014-240006

(51) Int. Cl.
*A61B 34/10* (2016.01)
*A61M 5/145* (2006.01)
(Continued)

(52) U.S. Cl.
CPC ............ *A61B 34/10* (2016.02); *A61B 5/0263* (2013.01); *A61B 6/037* (2013.01); *A61B 6/504* (2013.01);
(Continued)

(58) Field of Classification Search
CPC ......... A61B 5/0263; A61B 6/03; A61B 6/032; A61B 6/037; A61B 6/481; A61B 6/504;
(Continued)

(56) References Cited

U.S. PATENT DOCUMENTS 5,583,902 A    12/1996   Bae
5,687,208 A *  11/1997   Bae ..................... G06F 19/3468
                                                            378/8
(Continued)

FOREIGN PATENT DOCUMENTS

JP    2000-506398 A    5/2000
JP    2003-190148 A    7/2003
(Continued)

OTHER PUBLICATIONS

Google Patent Translation of JP2007151881A. Retrieved Jan. 17, 2019. https://patents.google.com/patent/JP2007151881A/en?oq=jp2007151881 (Year: 2019).*
(Continued)

*Primary Examiner* — Amanda K Hulbert
(74) *Attorney, Agent, or Firm* — Studebaker & Brackett PC

(57) ABSTRACT

In order to achieve a prediction approximating an actual change with time of a pixel value in a tissue with higher accuracy, provided is a simulator, which is configured to predict a change with time of a pixel value in a tissue of an object, including: an object information acquisition unit configured to acquire information on the object; a protocol acquisition unit configured to acquire an injection protocol
(Continued)

for a contrast medium; a tissue information acquisition unit configured to acquire information on the tissue; and a prediction unit configured to predict, based on the information on the object, the injection protocol, and the information on the tissue, a change with time of a pixel value of each of a plurality of compartments obtained by dividing the tissue along a blood flow direction.

15 Claims, 12 Drawing Sheets

(51) Int. Cl.
    *A61B 5/026*   (2006.01)
    *A61B 6/03*    (2006.01)
    *A61B 6/00*    (2006.01)
    *A61B 8/08*    (2006.01)
    *A61M 5/00*    (2006.01)
    *A61M 5/172*   (2006.01)

(52) U.S. Cl.
    CPC .............. *A61B 8/481* (2013.01); *A61M 5/007* (2013.01); *A61M 5/145* (2013.01); *A61M 5/172* (2013.01); *A61B 6/032* (2013.01); *A61B 2034/104* (2016.02); *A61M 2205/502* (2013.01)

(58) Field of Classification Search
    CPC ... A61B 8/481; A61B 34/10; A61B 2034/104; A61M 5/007; A61M 5/145; A61M 5/172; A61M 2205/502
    USPC .......................................................... 600/432
    See application file for complete search history.

(56) References Cited

U.S. PATENT DOCUMENTS

| 2003/0097076 | A1  | 5/2003  | Nambu et al. |
| 2007/0282263 | A1* | 12/2007 | Kalafut ............. A61M 5/14546 604/131 |
| 2008/0075344 | A1  | 3/2008  | Nambu et al. |
| 2012/0121145 | A1  | 5/2012  | Funabasama et al. |
| 2013/0211247 | A1  | 8/2013  | Kalafut |

FOREIGN PATENT DOCUMENTS

| JP |        3553968 B2  |   | 8/2004 |            |
| JP |   2007-151881 A    |   | 6/2007 |            |
| JP |    2007151881 A    | * | 6/2007 | ............. A61B 6/507 |
| JP |   2008-521506 A    |   | 6/2008 |            |
| JP |   2012-071124 A    |   | 4/2012 |            |
| JP |   2013-533028 A    |   | 8/2013 |            |

OTHER PUBLICATIONS

The International Preliminary Report on Patentability (Chapter I) and Translation of Written Opinion of the International Searching Authority; PCT/JP2015/005861; dated May 30, 2017.

International Search Report issued in PCT/JP2015/005861; dated Mar. 1, 2016.

Written Opinion issued in PCT/JP2015/005861; dated Mar. 1, 2016.

* cited by examiner

FIG. 4

| TISSUE | TISSUE VOLUME | CAPILLARY VESSEL VOLUME | EXTRACELLULAR FLUID SPACE VOLUME | BLOOD FLOW RATE PER UNIT TISSUE VOLUME (ARTERY BLOOD FLOW VELOCITY) | SEEP-OUT RATE (CAPILLARY PERMEABILITY-SURFACE AREA PRODUCT) | SEEP-BACK RATE (CAPILLARY PERMEABILITY-SURFACE AREA PRODUCT) |
|---|---|---|---|---|---|---|
| STOMACH | 120-160mL | 2-5mL | 12-18mL | 120-180mL/min | 15-25 | 15-25 |
| SPLEEN | 120-160mL | 10-15mL | 45-65mL | 150-250mL/min | 15-25 | 15-25 |
| PANCREAS | 120-150mL | 3-6mL | 30-50mL | 120-180mL/min | 15-25 | 15-25 |
| INTESTINAL TRACT | 1800-2000mL | 30-40mL | 500-600mL | 0.4-0.5mL/min | 150-250 | 150-250 |

FIG. 5
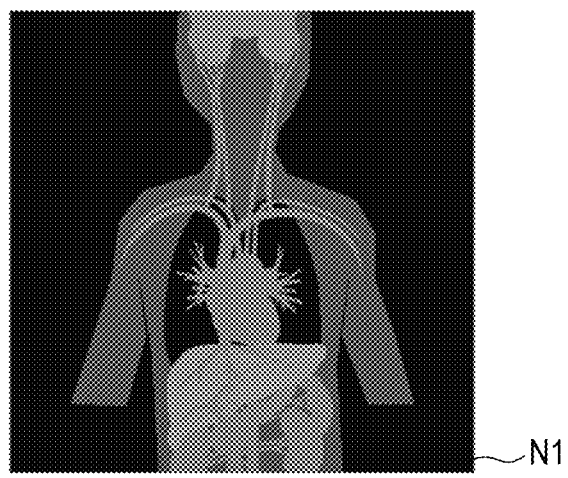
N1
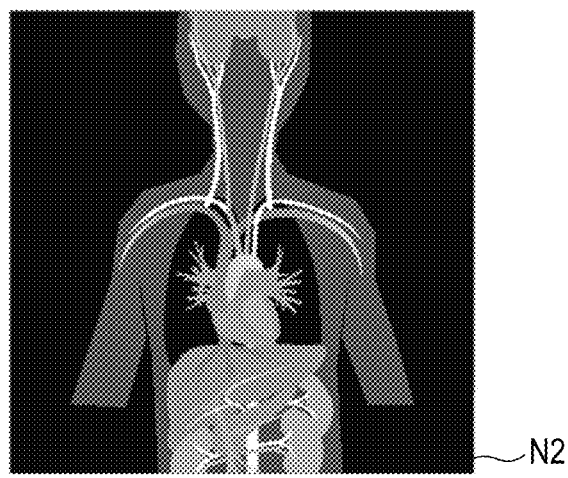
N2
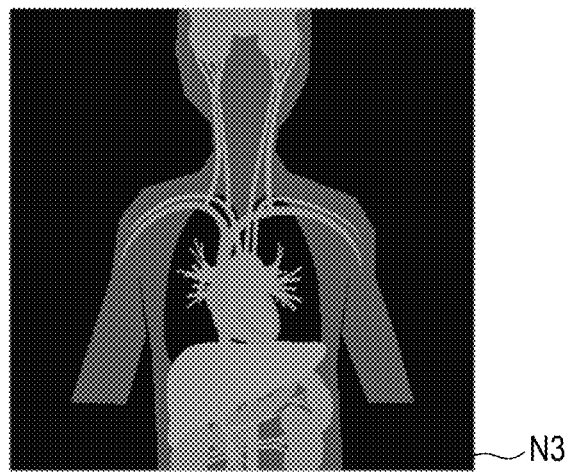
N3

FIG. 7
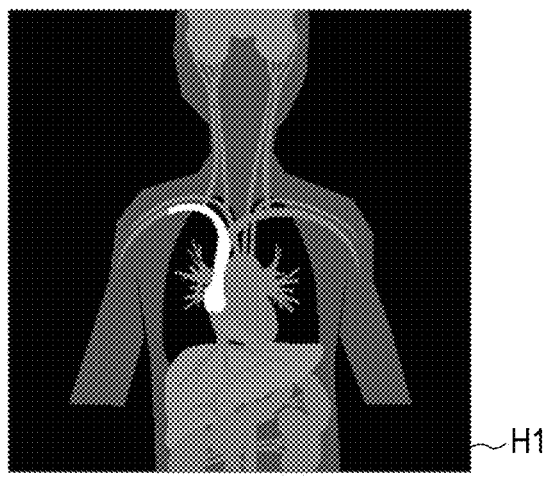
— H1
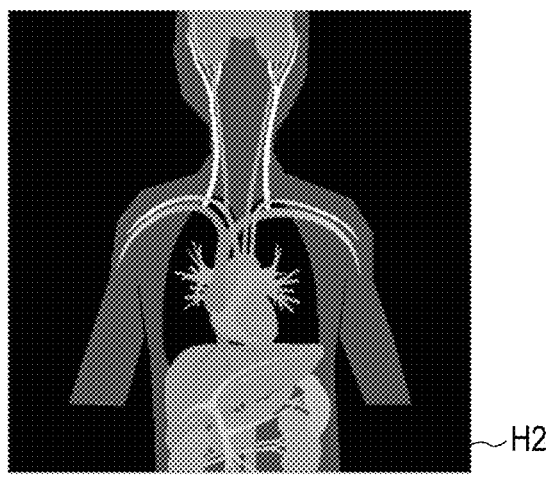
— H2
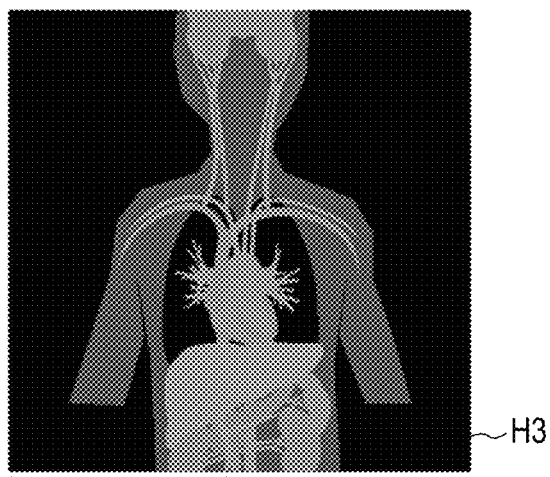
— H3

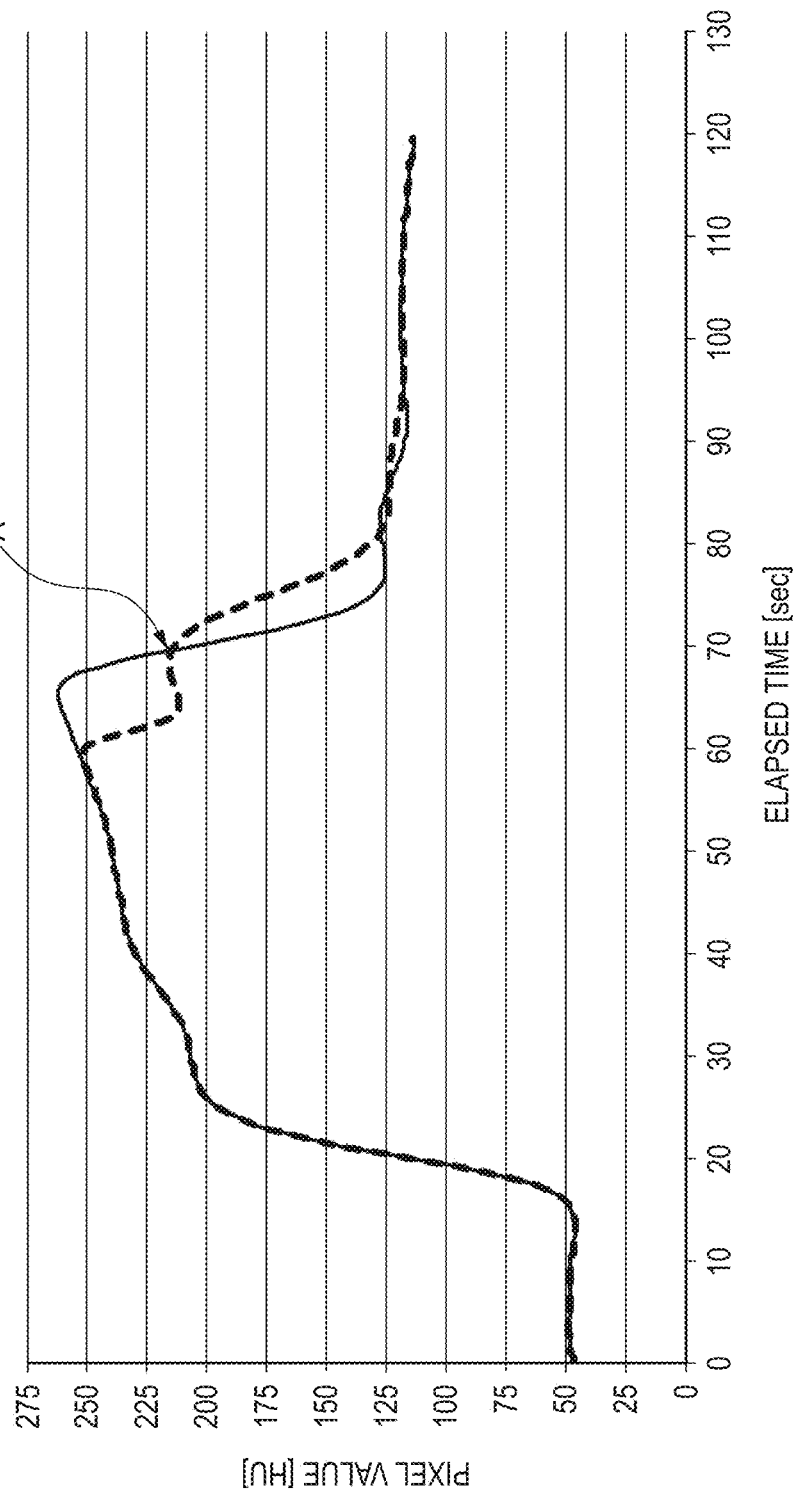

SIMULATOR, INJECTION DEVICE OR IMAGING SYSTEM PROVIDED WITH SIMULATOR, AND SIMULATION PROGRAM

TECHNICAL FIELD

The present invention relates to a simulator, which is configured to predict a change with time of a pixel value (CT value) of an image taken of a tissue of an object, an injection device or imaging system including the simulator, and a simulation program.

BACKGROUND ART

Hitherto, there has been known a method of using a computed tomography (CT) apparatus to take an image of a tissue of a patient as an object through enhancement with a contrast medium injected into a blood vessel. There has also been known a prediction method in which an enhanced level (pixel value) of a contrast intensity with the contrast medium is predicted based on body habitus features of the object and an injection protocol for the contrast medium. In addition, in the prediction method, a degree of enhancement of the contrast intensity in the tissue of the object is predicted as a function of elapse of time from an injection start time of the contrast medium (Patent Literature 1).

CITATION LIST

Patent Literature

PTL 1: Japanese Patent No. 3553968

SUMMARY OF INVENTION

Technical Problem

In the method disclosed in Patent Literature 1, it is assumed that the heart and a blood vessel form one compartment. It is also assumed that another organ forms one compartment including an intravascular space and an extracellular space. Then, in each compartment, a prediction is made assuming that a contrast medium is diffused over the entire compartment at the same time that the contrast medium reaches the compartment. However, in reality, a volume is different for each tissue, and hence a prediction result may be significantly different from an actual change in pixel value. In particular, when an injection amount of the contrast medium is small, when injection time period of the contrast medium is short, or when a density of the contrast medium is low, an actual diffusion rate in the tissue is low. Therefore, the prediction result tends to be significantly different from the actual change in pixel value.

Solution to Problem

In order to solve the above-mentioned problem, according to one embodiment of the present invention, there is provided a simulator, which is configured to predict a change with time of a pixel value in a tissue of an object, including: an object information acquisition unit configured to acquire information on the object; a protocol acquisition unit configured to acquire an injection protocol for a contrast medium; a tissue information acquisition unit configured to acquire information on the tissue; and a prediction unit configured to predict, based on the information on the object, the injection protocol, and the information on the tissue, a change with time of a pixel value of each of a plurality of compartments obtained by dividing the tissue along a blood flow direction.

Further, according to another embodiment of the present invention, there is provided an injection device, including: an injection head configured to inject a contrast medium in accordance with an injection protocol; and the above-mentioned simulator.

Further, according to another embodiment of the present invention, there is provided an imaging system, including: a medical imaging apparatus configured to take an image of an object; and the above-mentioned simulator.

Further, according to another embodiment of the present invention, there is provided a simulation program, which causes a computer to predict a change with time of a pixel value in a tissue of an object, the simulation program causing the computer to function as: an object information acquisition unit configured to acquire information on the object; a protocol acquisition unit configured to acquire an injection protocol for a contrast medium; a tissue information acquisition unit configured to acquire information on the tissue; and a prediction unit configured to predict, based on the information on the object, the injection protocol, and the information on the tissue, a change with time of a pixel value of each of a plurality of compartments obtained by dividing the tissue along a blood flow direction.

With the above-mentioned configuration, a prediction approximating the actual change with time of the pixel value in the tissue can be made with higher accuracy. In particular, when the injection amount of the contrast medium is small, when the injection time period of the contrast medium is short, or when the density of the contrast medium is low, the prediction can be made with high accuracy. Moreover, a position of the contrast medium in each tissue can be predicted. Therefore, optimal injection conditions or imaging conditions can be predicted before actual injection, and hence failure in taking an image of the tissue can be prevented.

Further features of the present invention are apparent from the following description of exemplary embodiments with reference to the attached drawings.

BRIEF DESCRIPTION OF DRAWINGS

FIG. 4 is a table for showing parameters of the stomach, spleen, pancreas, and intestinal tract.

FIG. 5 is diagrams of predicted images displayed on a display unit of the simulator.

FIG. 7 is diagrams of predicted images displayed on the display unit of the simulator when helical scan is selected.

FIG. 12 is a graph for showing time-density curves according to the modified embodiment.

DESCRIPTION OF EMBODIMENTS

Exemplary embodiments for carrying out the present invention are now described in detail with reference to the drawings. However, for example, the dimensions, materials, shapes, and relative positions of the components, which are described in the following embodiments, may be suitably set and changed based on the configuration of the apparatus to which the present invention is applied or based on various conditions. Unless otherwise noted, the scope of the present invention is not limited to the embodiments specifically described herein. In this specification, up and down correspond to an upward direction and a downward direction with respect to the direction of gravity, respectively.

First Embodiment

Figure 1:
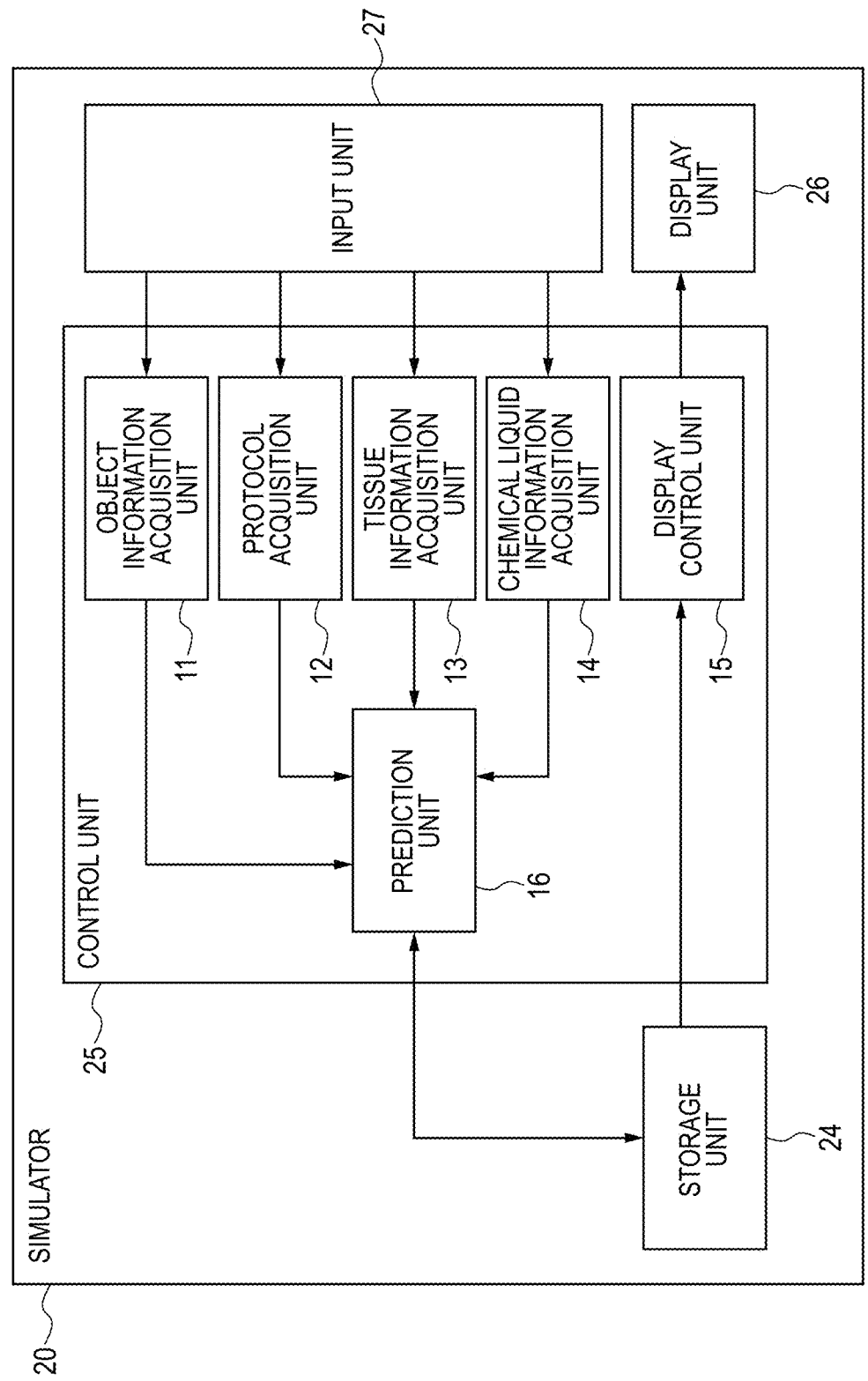
FIG. 1 is a schematic block diagram of a simulator.

As illustrated in FIG. 1, a simulator (perfusion simulator) 20, which is configured to predict a change with time of a pixel value in a tissue of an object, includes a prediction unit 16. The prediction unit 16 is configured to predict, based on information on the object, an injection protocol, and information on the tissue, a change with time, which is caused by at least a contrast medium, of a pixel value of each of a plurality of compartments obtained by dividing the tissue of the object along a blood flow direction. The pixel value is changed under effects of physiological saline, blood, and the like as well as the contrast medium.

The simulator 20 also includes an object information acquisition unit 11 configured to acquire the information on the object. The prediction unit 16 receives, from the object information acquisition unit 11, object information on a subject to be inspected serving as the object, such as an amount of hemoglobin (g/dL) and a body weight (kg) of the object. Here, the object information acquisition unit 11 acquires the object information input by an operator via an input unit 27 of the simulator 20.

Figure 8:
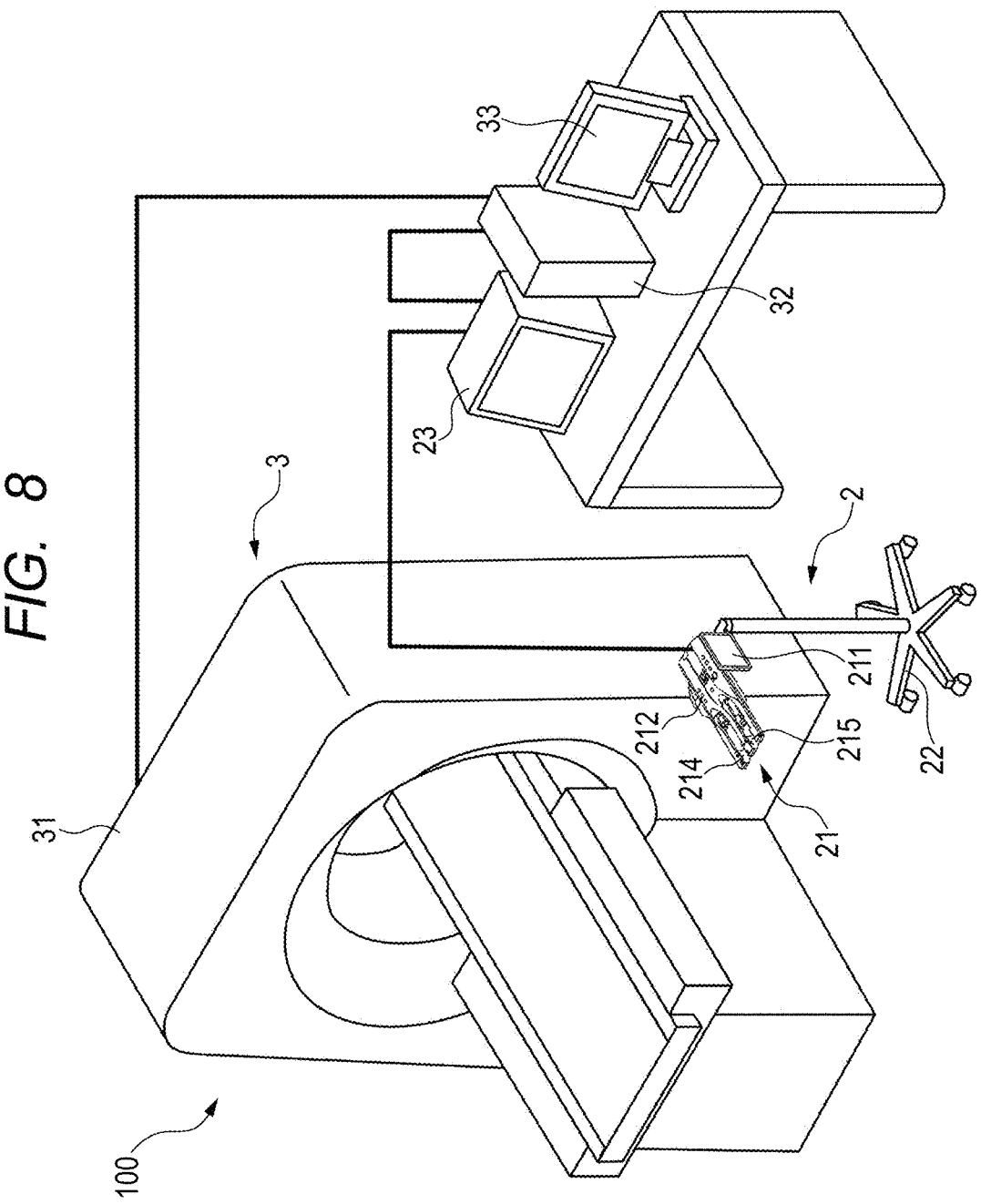
FIG. 8 is a schematic view of an injection device and an imaging system.

Alternatively, the object information acquisition unit 11 may acquire the object information from a storage unit 24 of the simulator 20 or an external storage device (server). Examples of such a server include a radiology information system (RIS), picture archiving and communication systems (PACS), a hospital information system (HIS), an image inspection system, and an image generation workstation. Further, the object information acquisition unit 11 may acquire the object information from an imaging apparatus 3 (FIG. 8) or an injection device 2 (FIG. 8). The object information may include a lean body mass, a circulating blood volume, a subject number (subject ID), the subject's name, sex, birth date, age, height, blood volume, blood flow velocity, and body surface area, and diseases of the subject, history of adverse drug reactions, creatinine value, heart rate, and cardiac output, and other such information.

The simulator 20 further includes a protocol acquisition unit 12 configured to acquire the injection protocol for the contrast medium. The prediction unit 16 acquires, from the protocol acquisition unit 12, the injection protocol, for example, a contrast medium injection velocity (mL/sec) and a contrast medium injection time period (sec). Here, the protocol acquisition unit 12 acquires the injection protocol input by the operator via the input unit 27. The injection protocol may include information on injection conditions, such as an injection method, a contrast medium injection position, an injection amount, an injection timing, a contrast medium density, and an injection pressure. Alternatively, the protocol acquisition unit 12 may acquire the injection protocol from the storage unit 24, the external storage device, or the injection device 2.

In particular, the contrast medium injection position may be input from an injection setting screen of the simulator 20, and in a normal case, an upper extremity vein is selected. As other injection positions, the hepatic artery (hepatic arteriography: CTHA), superior mesenteric artery (portography: CTAP), right ventricle, ascending aorta, and the like may be selected. Moreover, the injection protocol may include, in addition to a constant contrast medium injection velocity, presence or absence of pushing-injection for the contrast medium, an injection velocity of the physiological saline, injection time period of the physiological saline, increase or reduction in injection velocity, a volume of an injection tube, and other such information.

The simulator 20 further includes a tissue information acquisition unit 13 configured to acquire information on the tissue of the object. The prediction unit 16 acquires, from the tissue information acquisition unit 13, the number of compartments in the tissue (number of compartments with which the blood vessel and organ are divided), a volume of the tissue (volume of a vascular lumen), a volume of capillary vessels, a volume of an extracellular fluid space, a blood flow rate per unit tissue volume (blood flow velocity), a seep-out rate of the contrast medium in the tissue (capillary permeability-surface area product), a seep-back rate of the contrast medium in the tissue (capillary permeability-surface area product), pixel value inherent in the tissue, and other such tissue information.

Here, the tissue information acquisition unit 13 acquires the object information input by the operator via the input unit 27. The tissue includes the heart (right ventricle and left ventricle), blood vessel, and other organs and muscles. When the prediction unit 16 acquires the pixel value inherent in the tissue, a degree of enhancement with the contrast medium is predicted based on the pixel value inherent in each tissue. Alternatively, the tissue information acquisition unit 13 may acquire the tissue information from the storage unit 24, the external storage device, or the injection device 2.

The simulator 20 further includes a chemical liquid information acquisition unit 14 configured to acquire chemical liquid information on a chemical liquid. The prediction unit 16 acquires, from the chemical liquid information acquisition unit 14, a contrast medium density (mgI/mL), an amount of contrast medium (mL), a total amount of iodine (mgI), the half-life of the contrast medium (contrast medium discharge rate), and other such chemical liquid information. The prediction unit 16 may further calculate an amount of iodine per 1 kg of body weight (mgI/kg) based on the total amount of iodine and the body weight of the object. Here, the chemical liquid information acquisition unit 14 acquires the chemical liquid information input by the operator via the input unit 27. The chemical liquid information may include the product name, product ID, chemical classification, components, density, viscosity, expiration date, syringe capacity, withstanding pressure of the syringe, inner diameter of a cylinder, piston stroke, lot number, and the like.

Alternatively, the chemical liquid information acquisition unit 14 may acquire the chemical liquid information from the storage unit 24, the external storage device, or the injection device 2. Further, the chemical liquid information acquisition unit 14 may acquire the chemical liquid information from a reading unit included in the injection device 2. The reading unit reads a data carrier attached to the syringe mounted to an injection head. The data carrier is, for example, an RFID chip, an IC tag, or a barcode, and stores the chemical liquid information related to the chemical liquid.

The prediction unit 16 may also acquire inspection information, for example, a tube voltage (kVp), via the input unit 27. The inspection information may include an inspection number (inspection ID), site to be inspected, inspection date and time, chemical liquid type, chemical liquid name, imaging conditions (e.g., site to be imaged), and the like.

Further, the prediction unit 16 may acquire whether or not to consider regional perfusion (bolus transport), analysis time (sec), and other such additional information via the input unit 27. Here, the analysis time is a length of time for prediction, and corresponds to a length of an X axis of a graph (FIG. 6) for showing a time-density curve (TDC curve) 43. In addition, when the operator chooses to consider the regional perfusion, the prediction unit 16 considers seeping of the contrast medium out of the capillary vessels into the extracellular fluid space in the tissues.

Then, the prediction unit 16 predicts, based on the information on the object, the injection protocol, and the information on the tissue, the change with time of the pixel value for each of the plurality of compartments obtained by dividing the tissue along the blood flow direction. Thereafter, the prediction unit 16 stores, in the storage unit 24 of the simulator 20, the pixel value of each compartment at each time in association with each tissue.

The simulator 20 further includes a control unit 25, for example, a CPU. The storage unit 24, which stores a result of the prediction by the prediction unit 16, stores control programs and other such data. Then, the control unit 25 controls the simulator 20 in accordance with the control programs stored in the storage unit 24. Moreover, the control unit 25 includes the object information acquisition unit 11, the protocol acquisition unit 12, the tissue information acquisition unit 13, the chemical liquid information acquisition unit 14, and a display control unit 15 configured to control a display unit 26. The control unit 25 executes various kinds of processing in accordance with the control programs implemented in the storage unit 24, with the result that the respective units are logically realized as various functions.

The storage unit 24 also has stored therein a simulation program, which causes a computer (control unit) to predict the change with time of the pixel value in the tissue of the object. This simulation program causes the computer to function as the object information acquisition unit 11 configured to acquire the information on the object, the protocol acquisition unit 12 configured to acquire the injection protocol for the contrast medium, the tissue information acquisition unit 13 configured to acquire the information on the tissue, and the prediction unit 16 configured to predict, based on the information on the object, the injection protocol, and the information on the tissue, the change with time of the pixel value of each of the plurality of compartments obtained by dividing the tissue along the blood flow direction. The simulation program may be stored in a computer-readable storage medium.

Moreover, the storage unit 24 includes a random access memory (RAM), which is a system work memory used by the control unit 25 to operate, a read only memory (ROM), which is configured to store programs, system software, or the like, and a hard disk drive, for example. The control unit 25 may control the various kinds of processing in accordance with programs stored on a compact disc (CD), a digital versatile disc (DVD), a compact flash (CF) card, or other such portable storage media, or a server on the Internet or other such external storage media.

The simulator 20 further includes the display unit 26 configured to display the compartments of each tissue in colors of densities corresponding to pixel values. The display control unit 15 changes • light and shade of each of compartments of each tissue, which are displayed on the display unit 26, in accordance with changes with time of the pixel values. To that end, the display control unit 15 reads the pixel values of the compartments at a predetermined time from the storage unit 24 to change the light and shade of each of compartments. An operation screen, for example, an input screen, is displayed on the display unit 26. Various kinds of information, such as the injection protocol, an input state and setting state of the device, and an injection result may also be displayed.

Moreover, the input unit 27 of the simulator 20 is connected to the object information acquisition unit 11, the protocol acquisition unit 12, the tissue information acquisition unit 13, and the chemical liquid information acquisition unit 14. A keyboard or other such devices may be used as the input unit 27, but a touch panel may be used both as the input unit 27 and the display unit 26.

The above-mentioned simulator 20 may be mounted in an imaging system 100 including a medical imaging apparatus 3, or the injection device 2 configured to inject the contrast medium, which are illustrated in FIG. 8 to be described later. Alternatively, the simulator 20 may be mounted in an external computer that is wiredly or wirelessly connected to the imaging apparatus 3 or the injection device 2. As the imaging apparatus 3, various medical imaging apparatus, such as a magnetic resonance imaging (MRI) apparatus, a computed tomography (CT) apparatus, an angio imaging apparatus, a positron emission tomography (PET) apparatus, a single photon emission computed tomography (SPECT) apparatus, a CT angio apparatus, an MR angio apparatus, ultrasonic diagnostic equipment, and a blood vessel imaging apparatus may be used, for example. In this specification, a CT apparatus is described.

Figure 2:
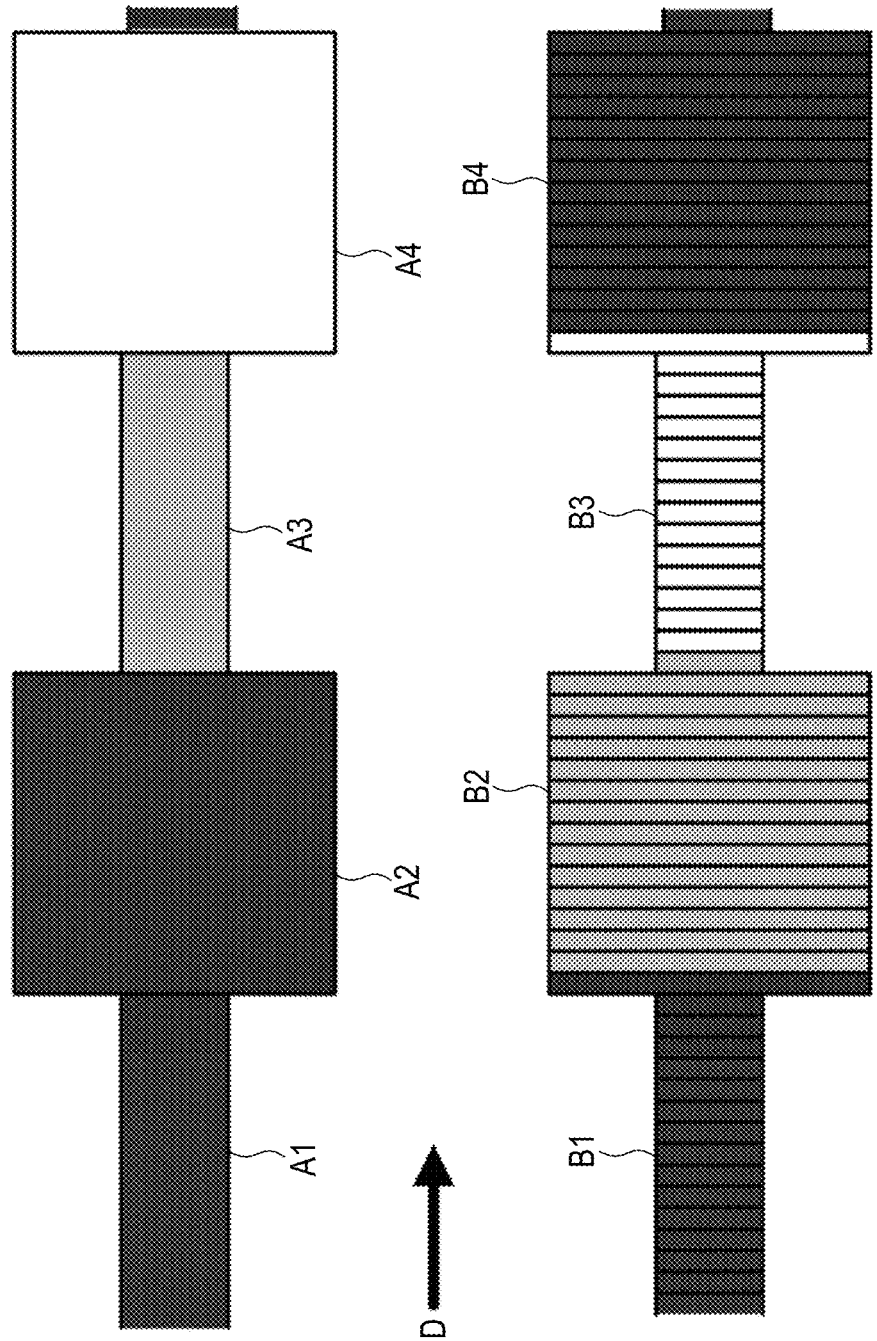
FIG. 2 is diagrams for illustrating a plurality of compartments according to a first embodiment of the present invention.

Next, referring to FIG. 2, the prediction of the change with time of the pixel value by the prediction unit 16 is described. On the upper side of FIG. 2, there is illustrated a schematic diagram in a case where each of a blood vessel A1, an organ A2, a blood vessel A3, and an organ A4, which are communicated in series in a blood flow direction D, respectively corresponds to one compartment. In this case, the prediction unit 16 makes a prediction assuming that the pixel value of the entirety of each tissue is changed immediately after the contrast medium reaches each of the tissues. Then, it is predicted that the pixel value of the entire tissue is changed irrespective of an actual diffusion rate or position of the contrast medium.

Specifically, in the organ A4 of FIG. 2, where the contrast medium has just arrived, a change in pixel value has not occurred in most of the organ A4 in reality, but the pixel value of the entire organ A4 is predicted to have increased (white). Moreover, in the blood vessel A3, the contrast medium has barely moved to the organ A4 in reality, but a pixel value of the entire blood vessel A3 is predicted to have been reduced (gray). Further, in the organ A2, where the contrast medium remains in reality, a pixel value of the entire organ A2 is predicted to have been reduced (black). Therefore, especially when the actual diffusion rate in the tissues is slow, the changes in pixel value of the tissues cannot be predicted accurately.

Meanwhile, on the lower side of FIG. 2, a schematic diagram according to a first embodiment of the present invention is illustrated. Each of a blood vessel B1, an organ B2, a blood vessel B3, and an organ B4, which are communicated in series in the blood flow direction D, is divided into a plurality of, that is, 15 compartments along the blood flow direction D. In other words, each tissue is divided into the plurality of compartments along the blood flow direction D in accordance with a division number of compartments of the tissue, which is acquired from the tissue information acquisition unit 13.

In this case, the prediction unit 16 makes a prediction for each compartment by dividing a volume of the tissue including compartments to be predicted, a capillary vessel volume of the tissue, and an extracellular fluid space volume of the tissue by the division number of compartments. For example, when the division number of compartments is 15, the prediction unit 16 predicts the changes with time of the pixel values based on values obtained by dividing each of the volume, the capillary vessel volume, and the extracellular fluid space volume of the tissue by 15.

Therefore, in the organ B4 where a change in pixel value has not occurred in most of the organ B4 in reality, a pixel value of only a compartment located on the blood vessel B3 side is predicted to have been increased (white). Similarly, in the blood vessel B3, the contrast medium has barely moved to the organ B4 in reality, and hence a pixel value of only a compartment located on the organ B2 side is predicted to have been reduced (gray). Further, in the organ B2, where the contrast medium remains in reality, a pixel value of only a compartment located on the blood vessel B1 side is predicted to have been reduced (black). As a result, even when the actual diffusion rate in the tissues is low, the changes in pixel value of the tissues can be predicted accurately.

Figure 3:
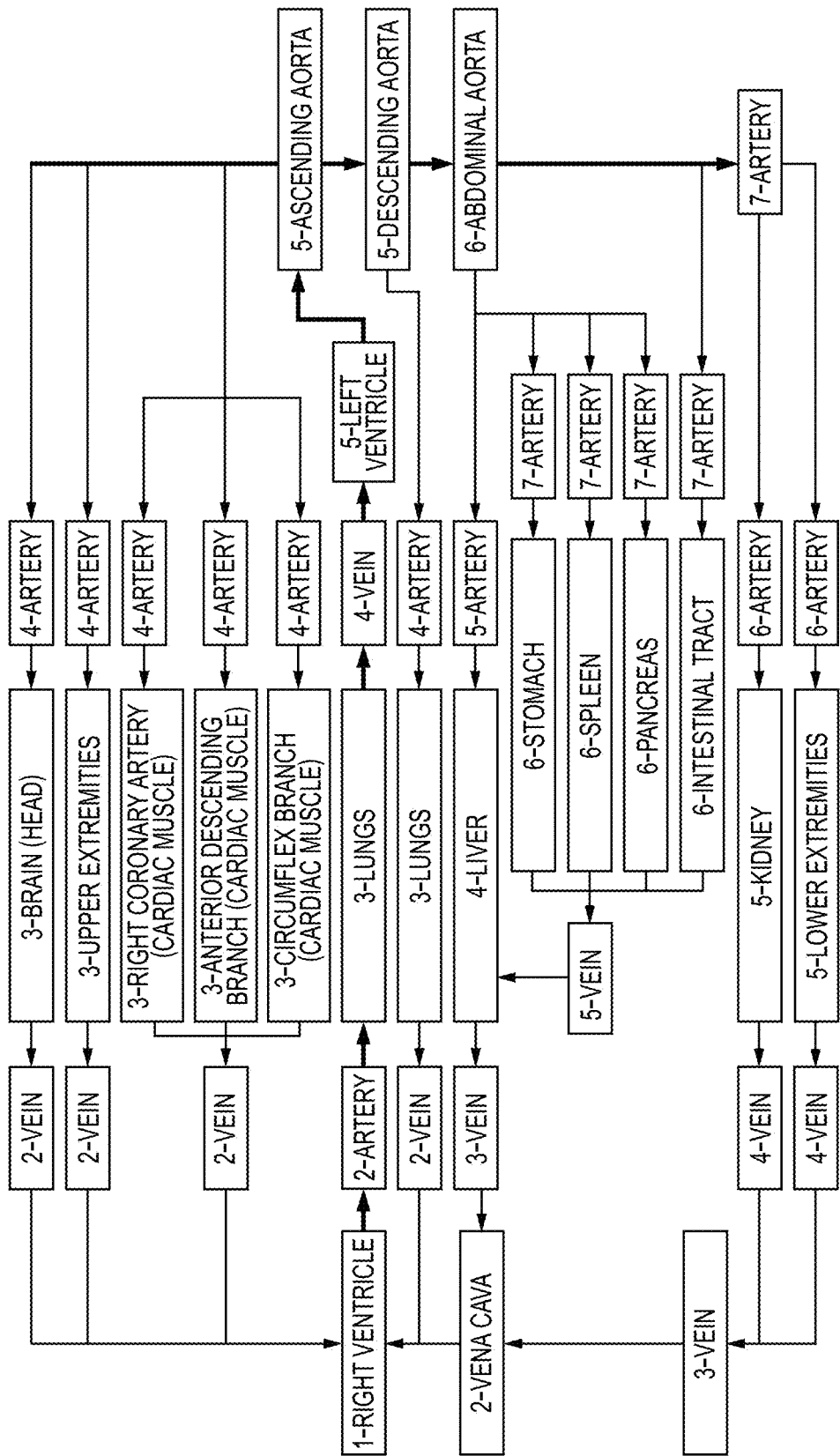
FIG. 3 is a diagram for illustrating a blood flow model.

Next, referring to FIG. 3, a specific prediction of a change in pixel value is described. As illustrated in FIG. 3, the tissues of the object in the first embodiment include right ventricle, aortas, vein, artery, brain (head), upper extremities, right coronary artery (cardiac muscle in which the right coronary artery is dominant), anterior descending branch (cardiac muscle in which the anterior descending branch is dominant), circumflex branch (cardiac muscle in which the circumflex branch is dominant), lungs, liver, stomach, spleen, pancreas, intestinal tract, kidneys, lower extremities, left ventricle, ascending aorta, descending aorta, and abdominal aorta. The contrast medium, which is injected from the upper extremity vein, moves to the respective organs through the right ventricle, lungs, left ventricle, and aortas (ascending aorta and descending aorta), and then reaches the right ventricle through veins. Then, the contrast medium, which has been injected into the body, is discharged out of the body through the kidneys.

The prediction unit 16 predicts the changes with time of the pixel values of the respective tissues in order of each of upstream and downstream from the right ventricle in the blood flow direction. In other words, the prediction unit 16 first makes a prediction for 1-right ventricle, and then makes predictions for a second tissue group including 2-vena cava and 2-veins, which are located on the upstream side of the right ventricle in the blood flow direction, and 2-artery, which is located on the downstream side of the right ventricle in the blood flow direction. Thereafter, the prediction unit 16 makes predictions in the following order: a third tissue group including the veins, brain, upper extremities, right coronary artery, anterior descending branch, circumflex branch, and lungs; a fourth tissue group including the arteries, veins, and liver; a fifth tissue group including the left ventricle, artery, ascending aorta, descending aorta, kidneys, and lower extremities; a sixth tissue group including the abdominal aorta, stomach, spleen, pancreas, intestinal tract, and arteries; and a seventh tissue group including the arteries. In FIG. 3, orders of predictions are indicated by the numbers prefixed to the names of the respective tissues via hyphens.

The prediction unit 16 may predict the changes with time of the pixel values of the tissues in order of each of upstream and downstream from the tissues close to the injection position of the contrast medium in the blood flow direction. For example, when the contrast medium is injected into the hepatic artery (CTHA), the prediction unit 16 may make a prediction for the liver first. Thereafter, the prediction unit 16 makes predictions for a tissue group including the artery, which is located on the upstream side of the liver in the blood flow direction, and the vein, which is located on the downstream side of the liver in the blood flow direction.

Moreover, in order to determine the change in pixel value in each of the tissues (blood vessels and organs) as a time function, the prediction unit 16 uses a differential equation, for example, Expression 1 below. In the expression, a density of the contrast medium entering a compartment is represented by $C_1$, a density of the contrast medium exiting the compartment is represented by $C_2$, a volume of the compartment is represented by V, and a blood flow rate per unit tissue volume (blood flow velocity) in the compartment is represented by Q.

$$V \cdot \frac{dC_2}{dt} = QC_1 - QC_2$$

Further, in order to determine changes of pixel values in tissues other than the right ventricle, left ventricle, and the blood vessels, the prediction unit 16 takes into consideration the seep-out rate of the contrast medium being transmitted from the capillary vessels to the extracellular fluid space, and the seep-back rate of the contrast medium being transmitted from the extracellular fluid space to the capillary vessels. Therefore, the prediction unit 16 uses differential equations, for example, Expressions 2 and 3 below. In the expressions, a volume of the extracellular fluid space is represented by Vec, a density of the contrast medium in the extracellular fluid space is represented by Cec, a volume of the capillary vessels is represented by Viv, a density of the contrast medium in the capillary vessels is represented by Civ, a seep-out rate is represented by $PS_1$, and a seep-back rate is represented by $PS_2$.

$$Vec \cdot \frac{dCec}{dt} = PS_1 Civ - PS_2 Cec$$

$$Viv \cdot \frac{dCiv}{dt} = (QC_1 - QCiv) - (PS_1 Civ - PS_2 Cec)$$

Then, the above-mentioned differential equations are solved to determine elapsed time and the changes in pixel values (contrast medium densities) from the start of injection as the time functions. As an example of parameters used for the prediction, in FIG. 4, values for the respective tissues: the stomach, spleen, pancreas, and intestinal tract are shown in a table. In the first embodiment, the prediction unit 16 predicts the changes with time of the pixel values while treating the stomach, spleen, pancreas, and intestinal tract as different tissues.

As shown in FIG. 4, for the stomach, a tissue volume of 120 mL or more and 160 mL or less, a capillary vessel volume of 2 mL or more and 5 mL or less, an extracellular fluid space volume of 12 mL or more and 18 mL or less, a blood flow rate per unit tissue volume (artery blood flow velocity) of 120 mL/min or more and 180 mL/min or less, a seep-out rate of 15 or more and 25 or less, and a seep-back rate of 15 or more and 25 or less are used.

Further, for the spleen, a tissue volume of 120 mL or more and 160 mL or less, a capillary vessel volume of 10 mL or more and 15 mL or less, an extracellular fluid space volume of 45 mL or more and 65 mL or less, a blood flow rate per unit tissue volume of 150 mL/min or more and 250 mL/min or less, a seep-out rate 15-25 of 15 or more and 25 or less, and a seep-back rate of 15 or more and 25 or less are used.

Further, for the pancreas, a tissue volume of 120 mL or more and 150 mL or less, a capillary vessel volume of 3 mL or more and 6 mL or less, an extracellular fluid space volume of 30 mL or more and 50 mL or less, a blood flow rate per unit tissue volume of 120 mL/min or more and 180 mL/min or less, a seep-out rate of 15 or more and 25 or less, and a seep-back rate of 15 or more and 25 or less are used.

Further, for the intestinal tract, a tissue volume of 1,800 mL or more and 2,000 mL or less, a capillary vessel volume of 30 mL or more and 40 mL or less, an extracellular fluid space volume of 500 mL or more and 600 mL or less, a blood flow rate per unit tissue volume of 0.4 mL/min or more and 0.5 mL/min or less, a seep-out rate of 150 or more and 250 or less, and a seep-back rate of 150 or more and 250 or less are used.

Here, the seep-out rate and the seep-back rate may be calculated based on a product of a capillary vessel area and a permeability. For example, assuming that a gross area of capillary vessels in a human body is 800 $m^2$, a capillary vessel area is assigned to each organ depending on its weight. Then, assuming that a permeability of every organ is 1 ml/min/g, the seep-out rate and the seep-back rate can be determined.

The prediction unit 16 has the prediction results sequentially stored in the storage unit 24 (FIG. 1). The prediction result includes information on the pixel values at each time associated with the tissues. Then, the display unit 26 (FIG. 1) schematically displays a predicted image of each tissue including the plurality of compartments. Further, the display control unit 15 reads the pixel values from the storage unit 24, and controls the display unit 26 so as to change the light and shade of each compartment in accordance with the change with time of the pixel value.

In FIG. 5, change of the light and shade in each predicted image as an example are illustrated, and FIG. 5 corresponds to horizontal cross sections of a body in a cephalocaudal direction. It should be noted, however, that unlike the actual cross section, all tissues are illustrated so that the respective tissues can be seen at a glance. Moreover, a window width of 350 and a window level of 40 are set. The window width corresponds to a contrast range of the pixel values, and the window level corresponds to a brightness of a screen. When the pixel value is smaller than a value obtained by subtracting half the value of the window width from the value of the window level, the display unit 26 displays in black. Moreover, when the pixel value is larger than a value obtained by adding half the value of the window width to the value of the window level, the display unit 26 displays in white.

On the upper side of FIG. 5, an image N1 of the tissues immediately after the contrast medium is injected into the upper extremity vein is illustrated, and the upper extremity vein is shown with its inherent pixel value (dark gray). Further, the contrast medium has not reached all the blood vessels including the abdominal aorta and celiac artery yet, and all the blood vessels are shown with their inherent pixel values (dark gray). Next, in the center of FIG. 5, an image N2 of the tissues after about 25 seconds have elapsed from the start of injection is illustrated, and the abdominal aorta, celiac artery, internal jugular vein, and the like, in particular, are colored in white. Meanwhile, the upper extremity vein is reduced in pixel value and shown in light gray because the contrast medium has flowed out in an early stage.

On the lower side of FIG. 5, an image N3 of the tissues after about 120 seconds have elapsed from the start of injection is illustrated. With the contrast medium having diffused and distributed uniformly over the blood vessels and the organs of the entire body, as compared to the image N2, the pixel values are reduced and shown in light gray overall.

Figure 6:
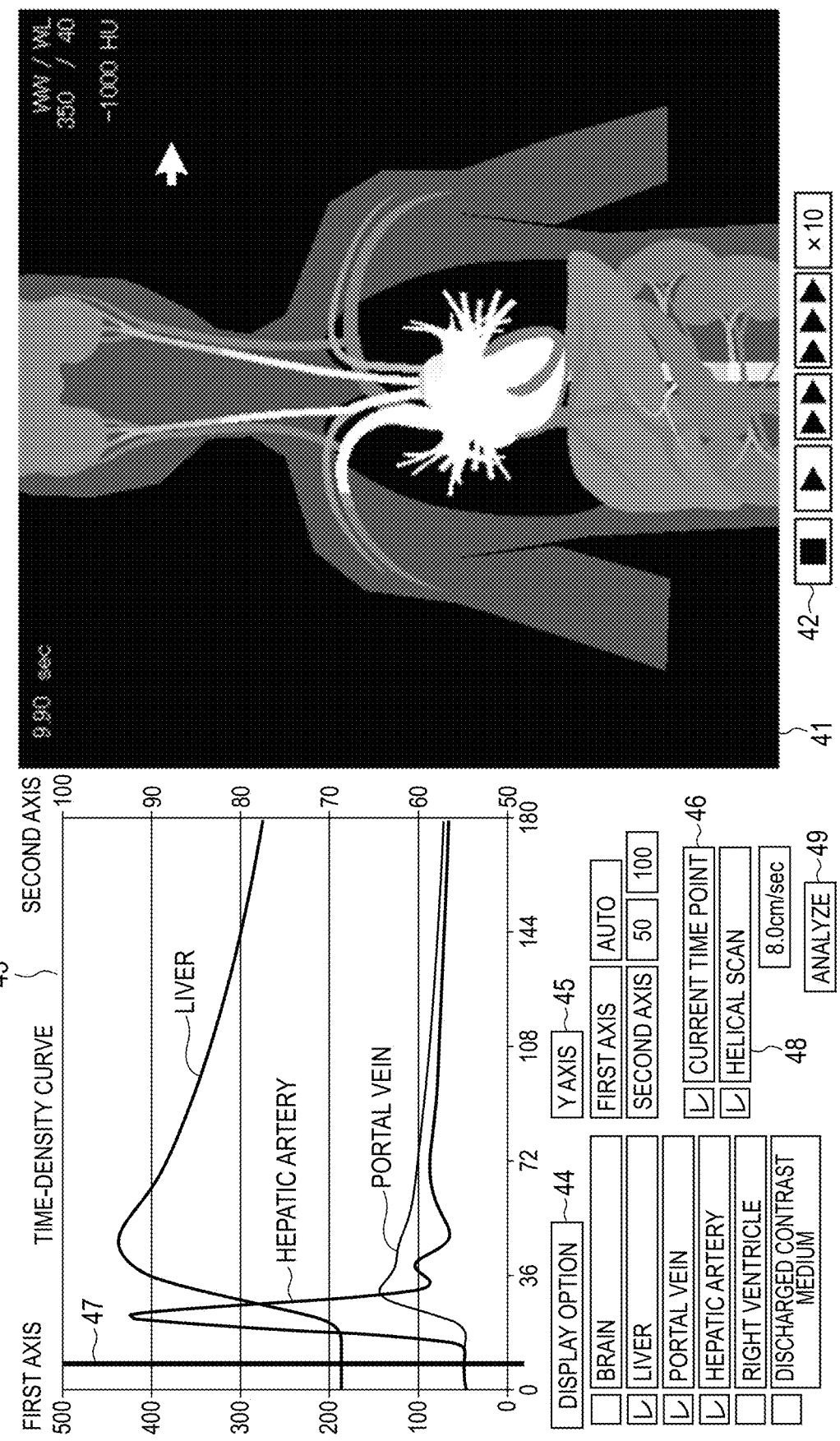
FIG. 6 is a diagram for illustrating an example of an operation screen displayed on the display unit.

Next, referring to FIG. 6, an operation screen as an example to be displayed on the display unit is described. As illustrated on the right side in FIG. 6, when the prediction by the prediction unit 16 is complete, the display control unit 15 reads, from the storage unit 24, a pixel value of each compartment at a predetermined time, for example, a time selected by the operator. Then, the display control unit 15 reflects the read pixel value on a predicted image 41 displays the predicted image 41 on the display unit 26. For example, in FIG. 6, a time point of 9.90 seconds is selected, and the predicted image 41 at the time point is displayed. In an initial setting, a predicted image 41 at the time of injection, that is, a time point of 0 seconds is displayed.

In the predicted image 41 of FIG. 6, a window width of 350 and a window level of 40 are set, and the respective values are displayed on the upper right corner of the predicted image 41. Moreover, below the window width and the window level, −1,000 HU is displayed as the pixel value. This indicates a pixel value at a position corresponding to a portion pointed by a pointer indicated by the arrow in the predicted image 41. The operator may input a window width (WW) and a window level (WL) via the input unit 27.

Below the predicted image 41, operation buttons 42 are displayed. The operation buttons 42 include, in order from the left in FIG. 6, a stop button, a play button, a 2× speed play button, a 3× speed play button, and a 10× speed play button. When the operator selects the play button, the predicted images 41 are sequentially played as a moving image along the elapsed time. As a result, the operator may visually recognize the position of the contrast medium in each tissue at a desired time.

On the left side of the predicted image 41, the time-density curve 43 is displayed. In this time-density curve 43, an X axis (horizontal axis) corresponds to the elapsed time from the start of injection, and a Y axis (vertical axis) corresponds to the pixel value. Moreover, the Y axis includes the first axis and the second axis so that a plurality of tissues may be displayed on one graph. For example, in FIG. 6, time-density curves for the liver, portal vein, and hepatic artery are displayed.

The operator may select the tissues displayed on the time-density curve 43 via a display option 44, which is located on the lower side of the time-density curve 43. For example, in FIG. 6, the liver, portal vein, and hepatic artery are selected from among the brain, liver, portal vein, hepatic artery, and right ventricle. Moreover, an amount of contrast medium discharged from inside the body may also be displayed. Examples of other tissue that may be selected include the upper extremity, lungs, left ventricle, myocardium, right coronary artery, anterior descending branch, circumflex branch, bronchus, spleen, intestinal tract, kidneys, lower extremity, pancreas, pulmonary artery, pulmonary vein, ascending aorta, descending aorta, abdominal aorta, coeliac trunk, superior mesenteric artery, lower abdominal aorta, hepatic vein, renal artery, renal vein, cerebral artery, cerebral vein, upper extremity artery, upper extremity vein, lower extremity artery, lower extremity vein, superior vena cava, and inferior vena cava.

Moreover, on the right side of the display option 44, a Y axis input box 45 is displayed. In the Y axis input box 45, the operator may select an automatic setting, or input a desired value. For example, in FIG. 6, the automatic setting is selected for the first axis, and the maximum value and the minimum value of the first axis are set automatically. Moreover, for the second axis, 100 is input as the maximum value, and 50 is input as the minimum value.

Moreover, on the lower side of the Y axis input box 45, a current time point box 46 is displayed. When the operator selects the current time point box 46, a current time point bar 47 is displayed on the time-density curve 43. This current time point bar 47 indicates a time corresponding to the predicted image 41 (in FIG. 6, 9.90 seconds). When the predicted images 41 are played sequentially, the current time point bar 47 is moved along the X axis in accordance with the elapsed time.

Further, on the lower side of the current time point box 46, a helical scan box 48 is displayed. The operator may select the helical scan box 48 to input a bed moving speed (cm/sec). In FIG. 6, a bed moving speed of 8.0 cm/sec is input.

When the helical scan box 48 is selected, the display control unit 15 acquires delay time caused by helical scan. Here, the delay time corresponds to the elapsed time (movement time of the bed) from when the head is imaged to when each tissue is imaged, and is determined based on a length from an upper end of the predicted image 41 to each of the tissues. Then, the display control unit 15 reads, from the storage unit 24, a pixel value at a time obtained by adding the delay time to the predetermined time. In other words, the display control unit 15 reads the pixel value of each tissue at the time obtained by adding the acquired delay time to the predetermined time (current time point). For example, in the predicted image 41 of FIG. 6, the head (brain) indicates the pixel value at a time point when 9.90 seconds have elapsed, which is the current time point, and the right ventricle indicates the pixel value at a time point when 14.90 seconds have elapsed.

As a result, there may be obtained a predicted image in the case where the helical scan is performed. For example, when the current time point is set to a time point immediately after the start of injection (0 seconds), a pixel value immediately after the start of injection may be shown for the brain, a pixel value at a time point when 5 seconds have elapsed from the start of injection may be shown for the right ventricle, and a pixel value at a time point when 7.5 seconds have elapsed from the start of injection may be shown for the liver. The display control unit 15 may acquire the delay time through calculation. Alternatively, delay time associated with the bed moving speed may be stored in the storage unit 24 in advance, and the display control unit 15 may acquire the delay time from the storage unit 24.

The predicted images obtained as described above are described with reference to FIG. 7. In FIG. 7, changes in light and shade of the predicted images as an example in the case of the helical scan are illustrated. The images of FIG. 7 each correspond to a horizontal cross section of a body in the cephalocaudal direction, but all tissues are illustrated unlike the actual cross section. Moreover, a window width of 350 and a window level of 40 are set.

On the upper side of FIG. 7, an image H1 of the tissues immediately after the contrast medium is injected into the upper extremity vein is illustrated. However, unlike the image N1 of FIG. 5, for the upper extremity vein, a pixel value at the time point after the delay time is added is shown. Therefore, the upper extremity vein is colored in white due to the contrast medium. The contrast medium has not reached the other blood vessels yet, and the other blood vessels are shown with the inherent pixel value (deep gray).

Next, in the center of FIG. 7, an image H2 of the tissues at a time when about 25 seconds have elapsed from the start of injection is illustrated, and the internal jugular vein is colored in white because the contrast medium has arrived. However, unlike the image N2 of FIG. 5, pixel values at the time point after the delay time is added is shown, and hence for the abdominal aorta and celiac artery from which the contrast medium has already exited, the pixel values are reduced and shown in light gray. Moreover, the contrast medium has circulated to arrive at the portal vein, and hence the portal vein is colored in white.

On the lower side of FIG. 7, an image H3 of the tissues after about 120 seconds have elapsed from the start of injection is illustrated, and with the contrast medium having been diffused and distributed uniformly over the blood vessels and the organs of the entire body, the pixel value is reduced and shown in light gray overall as compared to the image H2.

Returning to the description of FIG. 6, on the lower side of the helical scan box 48, an "analyze" button 49 is displayed. When the operator selects the "analyze" button 49, the prediction unit 16 starts the prediction of the pixel values. The prediction unit 16 may start the prediction of the pixel values when the object information, the injection protocol, and the tissue information are acquired.

Next, referring to FIG. 8, the imaging system 100 including the simulator 20 is described. The imaging system 100 includes the injection device 2 configured to inject the contrast medium, and the medical imaging apparatus 3, which is connected wiredly or wirelessly to the injection device 2 and is configured to take an image of the object. The injection device 2 or the imaging apparatus 3 includes the above-mentioned simulator 20.

The imaging apparatus 3 includes an imaging unit 31 configured to take an image of the subject to be inspected in accordance with an imaging plan, a controller 32 configured to control the entire imaging apparatus 3, and a display 33, which serves as the display unit 26. The controller 32 and the display 33 may be formed integrally. Moreover, the imaging apparatus 3 is wiredly or wirelessly connected to the injection device 2, for example, via a gateway device (not shown).

The imaging plan for the imaging apparatus 3 may include the site to be imaged, an effective tube voltage, a model name, a manufacturer name, imaging time, a tube voltage, an imaging range, a rotation speed, a helical pitch, exposure time, dose, an imaging method, and other such information. The controller 32 controls the imaging unit 31 in accordance with the imaging plan to take the image of the subject to be inspected. Moreover, the controller 32 is connected to the display 33, and the input state and setting state of the apparatus, an imaging result, and various information are displayed on the display 33, for example.

The imaging unit 31 includes the bed, an X-ray source configured to irradiate the subject to be inspected serving as the object with an X ray, an X-ray detector configured to detect the X ray that has passed through the subject to be inspected, and other such components. The imaging unit 31 exposes the subject to be inspected to the X ray, and an inside of the body of the subject to be inspected is back-projected based on the X ray that has passed through the subject to be inspected to take a fluoroscopic image of the subject to be inspected. The imaging unit 31 may take the image using a radio wave or an ultrasonic wave instead of the X ray. Moreover, the controller 32 may communicate wiredly or wirelessly to/from the imaging unit 31, the injection device 2, and the like.

The injection device 2, which is configured to inject the contrast medium, injects a chemical liquid filled in the syringe, for example, various kinds of contrast media, the physiological saline, and other such chemical liquids into the body of the subject to be inspected serving as the object. Moreover, the injection device 2 includes an injection head 21 configured to inject the contrast medium in accordance with the injection protocol. The injection device 2 further includes a stand 22 configured to hold the injection head 21, and a console 23, which is connected wiredly or wirelessly to the injection head 21.

The console 23 functions as a controller that is configured to control the injection head 21, and also functions as the simulator 20. Moreover, the console 23 includes a touch panel, which functions as the input unit 27 and the display unit 26, and may communicate wiredly or wirelessly to/from the injection head 21, the imaging apparatus 3, and the like. The injection device 2 may include, instead of the touch panel, a display, which serves as the display unit 26, and a user interface, for example, a keyboard, which serves as the input unit 27.

Moreover, the simulator 20, the input unit 27, and the display unit 26 may be formed separately from each other. For example, the injection device 2 may include, instead of the console 23, a controller that is connected to the injection head 21, and the display unit 26 (e.g., touch panel display), which is connected to the controller and is configured to display an injection status of the chemical liquid, and other such information. Such a controller also functions as the simulator 20. Moreover, the injection head 21 and the controller may be formed integrally with the stand 22. Moreover, a ceiling hanging member may be provided instead of the stand 22 to hang the injection head 21 from the ceiling via the ceiling hanging member.

Moreover, the injection device 2 may include a power supply or battery, a hand switch connected to the console 23, a remote operation device, which is used to remotely operate the injection head 21, and other such components. The remote operation device may be used to remotely operate the injection head 21 to start or stop the injection. Moreover, the power supply or battery may be provided to any one of the injection head 21 and the controller (console 23), or may be provided separately from the injection head 21 and the controller (console 23).

The injection head 21 includes a first holding portion 214, on which a syringe filled with the contrast medium is mounted, and a second holding portion 215, on which a syringe filled with the physiological saline, which serves as a chemical liquid for pushing the contrast medium, is mounted. The injection head 21 also includes a drive mechanism (not shown) configured to push out the chemical liquid in the syringe mounted on the first holding portion 214 in accordance with the injection protocol, and a drive mechanism (not shown) configured to push out the chemical liquid in the syringe mounted on the second holding portion 215 in accordance with the injection protocol.

The injection head 21 further includes a head display 211, on which the injection conditions, the injection status, the input state and setting state of the apparatus, various injection results, and other such information are displayed, and an operation unit 212, which is used to input operations of the drive mechanisms. The head display 211 may be omitted. Alternatively, by being formed of a touch panel or the like, the head display 211 may also be used as the operation unit 212.

On the operation unit 212, a forward movement button for the drive mechanism, a backward movement button for the drive mechanism, a final confirmation button, and the like are provided. When the chemical liquid is injected, a mixing tube or the like is connected to a distal end portion of the syringe mounted on the injection head 21. When preparations for injection, such as connecting the mixing tube, are complete, the operator pushes the final confirmation button. As a result, the injection head 21 waits in a state of being ready to start the injection.

Thereafter, the chemical liquid pushed out of the syringe is injected into the body of the subject to be inspected through the mixing tube or the like. The mixing tube functions as a mixer for the contrast medium and a diluting chemical liquid. Examples of such a mixer include "SPIRAL FLOW (trademark)" manufactured by Nemoto Kyorindo co., Ltd.

On the injection head 21, various syringes, such as a prefilled syringe including the data carrier, for example, the RFID chip, the IC tag, or the barcode may be mounted, for example. The injection head 21 includes the reading unit (not shown), which is configured to read the data carrier attached to the syringe. In the data carrier, the chemical liquid information related to the chemical liquid is stored.

The injection device 2 is capable of receiving information from the server (external storage device), which is not shown, via an internal or external gateway device, and of transmitting information to the server. Moreover, the imaging apparatus 3 is capable of receiving information from the server, and of transmitting information to the server. In the server, an inspection order is stored in advance. The inspection order contains the object information on the subject to be inspected, and the inspection information on details of the inspection. The server may also store information on the imaging result, for example, data of an image transmitted from the imaging apparatus 3, and information on the injection result transmitted from the injection device 2.

With the above-mentioned imaging apparatus 3 including the simulator 20, the operator can operate the imaging apparatus 3 while checking the predicted image 41 on the display 33. Alternatively, the imaging apparatus 3 may change the imaging plan depending on the result of the prediction by the prediction unit 16. For example, when the operator inputs a desired pixel value to the imaging apparatus 3, and when the desired pixel value is different from a pixel value predicted by the prediction unit 16 of a tissue to be imaged, the imaging apparatus 3 may change the tube voltage, a tube current, or the like so that the prediction result matches the desired pixel value.

Moreover, with the injection device 2 including the simulator 20, the operator can operate the injection device 2 while checking the predicted image 41 on the console 23. Alternatively, the injection device 2 may change the injection protocol depending on the result of the prediction by the prediction unit 16. For example, when the operator inputs a desired pixel value to the injection device 2, and when the desired pixel value is different from a pixel value predicted by the prediction unit 16 of a tissue to be imaged, the injection device 2 may change the injection velocity, the injection time period, or the like so that the prediction result matches the desired pixel value.

According to the first embodiment of the present invention described above, the prediction approximating the changes with time of the pixel values in the actual tissues can be made with higher accuracy. In particular, when the injection amount of the contrast medium is small, when the injection time period of the contrast medium is short, or when the density of the contrast medium is low, the prediction can be made with high accuracy. In addition, the position of the contrast medium in each tissue can be predicted. Further, the operator can visually recognize the position of the contrast medium in each tissue at a desired time.

Moreover, according to the first embodiment of the present invention, even when the injection protocol includes pushing the injection of the contrast medium, an increase or reduction in injection velocity, or the like, the pixel value of each tissue can be predicted. For example, even in a case of a so-called cross-injection method, in which the injection velocity of the contrast medium is gradually reduced, and at the same time, the injection velocity of the physiological saline is increased, an image to be actually taken can be predicted. Further, when a new injection protocol or imaging plan is generated, an image to be actually taken can be predicted.

Second Embodiment

A second embodiment of the present invention is described with reference to FIG. 9. In the first embodiment, each of the tissues is divided into the same number of compartments. In contrast, in the second embodiment, a tissue having a large volume is divided into a larger number of compartments. In other words, the prediction unit 16 according to the second embodiment predicts a change with time of a pixel value in each of a plurality of compartments obtained by dividing a tissue (first tissue) having a small volume, and predicts a change with time of a pixel value in each of a plurality of compartments obtained by dividing a tissue (second tissue) having a large volume by a number larger than the number by which the tissue having the small volume is divided.

In the description of the second embodiment, differences from the first embodiment are described. The components described in the first embodiment are denoted by the same reference symbols, and descriptions thereof are therefore omitted. Unless otherwise noted, the components denoted by the same reference symbols each have substantially the same operation and function, and actions and effects thereof are also substantially the same.

Actual organs have mutually different volumes. For example, a volume of an organ A8 in FIG. 9 is several times larger than a volume of an organ A6. Therefore, a volume of each compartment of the organ A8 is several times larger than a volume of each compartment of the organ A6. When a prediction is made similarly to the first embodiment, in the predicted image 41, even a change in pixel value of one compartment is shown as a small change (movement distance of the contrast medium is short) in the organ A6. In contrast, in the organ A8, the change is shown as a big change (movement distance of the contrast medium is long) as compared to the organ A6. As a result, it becomes difficult for the operator to visually and correctly recognize the position of the contrast medium in each tissue.

To address this problem, in the second embodiment, the tissue having the large volume is divided into the number of compartments that is larger than that of the tissue having the small volume. Specifically, in FIG. 9, an organ B6 is divided into three compartments, and an organ B8 is divided into fifteen compartments. As a result, volumes of compartments of the organ B6 and the organ B8 approximate to each other, and hence the operator can visually and correctly recognize the position of the contrast medium in each tissue.

In the second embodiment described above, optimal division numbers of compartments are determined in advance depending on the volumes of the respective tissues, and are stored in the storage unit 24. The tissue information acquisition unit 13 acquires the division numbers of compartments from the storage unit 24, and the prediction unit 16 predicts the changes in pixel values based on the acquired division numbers of compartments.

According to the second embodiment of the present invention described above, the prediction approximating the changes with time of the pixel values in the actual tissues can be made with higher accuracy. In particular, when the injection amount of the contrast medium is small, when the injection time period of the contrast medium is short, or when the density of the contrast medium is low, the prediction can be made with high accuracy. In addition, the position of the contrast medium in each tissue can be predicted. Further, the operator can visually recognize the position of the contrast medium in each tissue at a desired time.

In addition, according to the second embodiment of the present invention, even when the tissue having the large volume and the tissue having the small volume are included in the predicted image 41, the operator can visually and correctly recognize the position of the contrast medium in each tissue.

Figure 9:
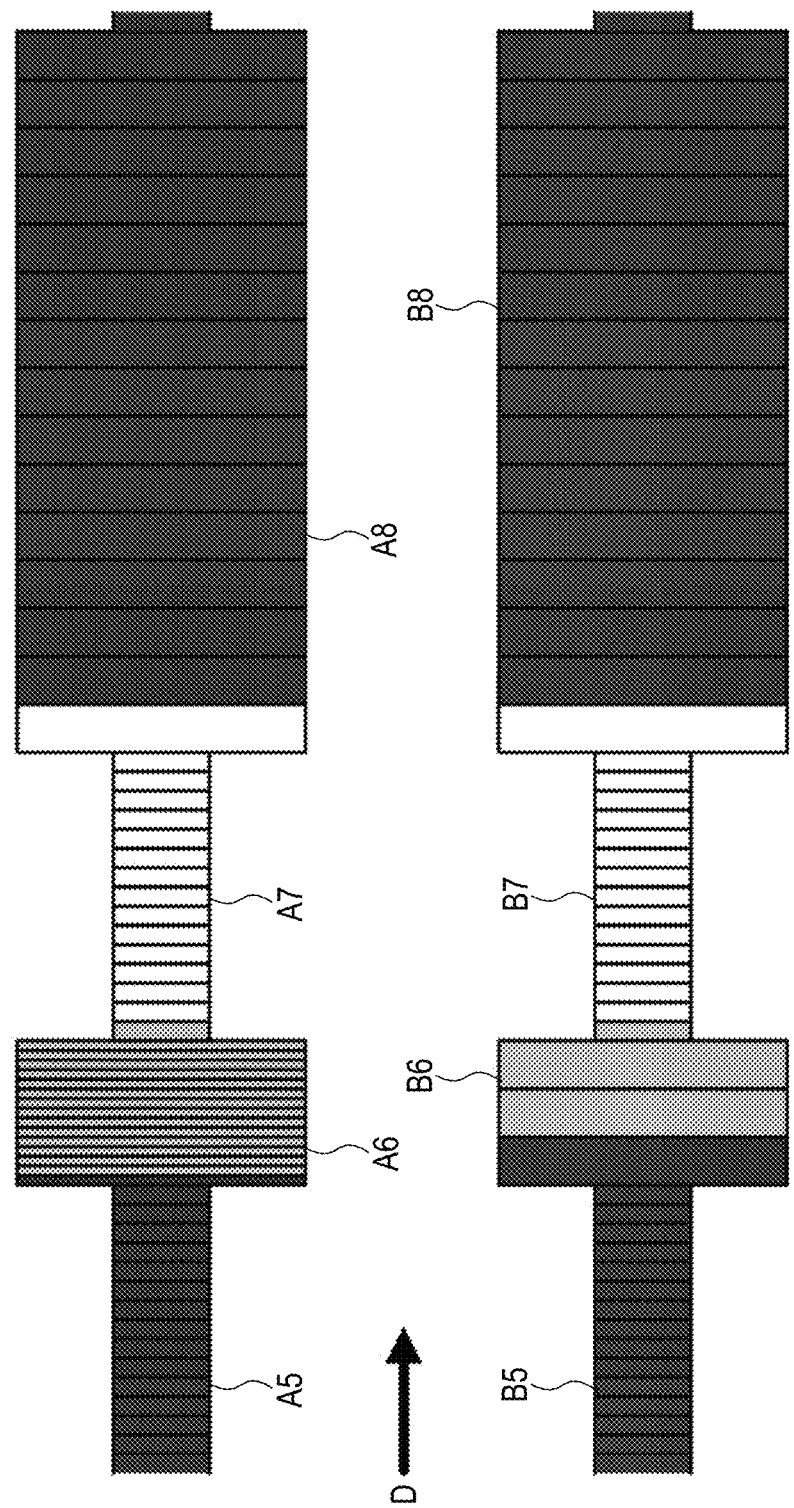
FIG. 9 is diagrams for illustrating a plurality of compartments according to a second embodiment of the present invention.

In FIG. 9, each of a blood vessel A5, a blood vessel A7, a blood vessel B5, and a blood vessel B7 is divided by the same number, that is, into fifteen compartments. However, a blood vessel having a large volume may be divided into a larger number of compartments as compared to a blood vessel having a small volume. In addition, the division numbers of compartments may be set so that volumes of compartments of a tissue B8 having a large volume and a tissue B6 having a small volume approximately match each other.

The present invention has been described above with reference to the embodiments, but the present invention is not limited to the above-mentioned embodiments. An invention modified without departing from the present invention, and an invention equivalent to the present invention are encompassed by the present invention. Moreover, the above-mentioned embodiments and modified embodiments may be combined as appropriate without departing from the present invention.

For example, the display unit 26 may display not only the horizontal cross section of the body, but also the predicted image 41 of a coronal section. Moreover, the division number of compartments of a tissue is not limited to 15, and an appropriate number of 2 or more is selected.

Moreover, noise information of the pixel value may be stored in the storage unit 24 in advance, and the display control unit 15 may read the noise information from the storage unit 24, and add the noise information to the predicted image 41 of each compartment. Examples of the noise information include an image for showing radial noise generated between the tissues colored in white due to the contrast medium. The image for showing the noise may be added by being superimposed on the predicted image 41 to obtain the predicted image 41 more approximating the image to be actually taken.

In each of the above-mentioned embodiments, the display unit 26 arranges compartments so as to form a schematic diagram in which a plurality of tissues are continuous in the blood flow direction, and displays each compartment in a color having a density corresponding to the pixel value. However, the display unit 26 may arrange the compartments so that each tissue is displayed alone, and display each compartment in a color having a density corresponding to the pixel value. Moreover, the display control unit 15 may control the display unit 26 so that numbers of compartments in the tissues are different. In this case, the display control unit 15 has each tissue displayed so as to include the number of compartments set by the operator, or the number of compartments stored in the storage unit 24 in advance. The display unit 26 may display each compartment in a color other than black and white.

Moreover, the injection head 21 is not limited to the type holding two syringes, but may be of a type including three or more syringe holding portions, or a type including only one syringe holding portion. Further, in the predicted image 41 illustrated in FIG. 6, when a predetermined tissue reaches the maximum pixel value, the display control unit 15 may display the read maximum pixel value on an image of the predetermined tissue or in the vicinity of the image of the predetermined tissue. For example, when the liver, portal vein, and hepatic artery are selected in the display option 44, the display control unit 15 may display the maximum pixel value of each of the selected tissues in the vicinity of the liver, portal vein, and hepatic artery in the predicted image 41. The maximum pixel value may be displayed in a color other than black and white, for example, in blue, green, red, or yellow.

Moreover, in the predicted image 41 illustrated in FIG. 6, the display control unit 15 may display each tissue (compartment) in a color other than a shade (gray scale) of black and white, for example, in a shade of blue, green, red, or yellow. Further, the display control unit 15 may display a predetermined tissue in a shade of a color other than black and white. For example, when the liver, portal vein, and hepatic artery are selected in the display option 44, the display control unit 15 may display the liver, portal vein, and hepatic artery in the predicted image 41 in shades of red, blue, and green, respectively.

Modified Embodiment

The prediction unit 16 may consider a change in blood flow rate per unit tissue volume (blood flow velocity) caused by the injection of the chemical liquid. In other words, when the chemical liquid is injected, in the tissues (compartments) downstream from the injection position in the blood flow direction, the blood flow velocity is changed by being pushed by the injected chemical liquid. In particular, when the chemical liquid is injected at a velocity that is higher than a normal blood flow velocity, the blood flow velocity is increased in the downstream tissues. To address this problem, when the injection velocity of the chemical liquid is higher than the normal blood flow velocity, the prediction unit 16 may consider the increase in blood flow velocity by adding, to the blood flow velocity, a difference obtained by subtracting the blood flow velocity from the injection velocity.

Figure 10:
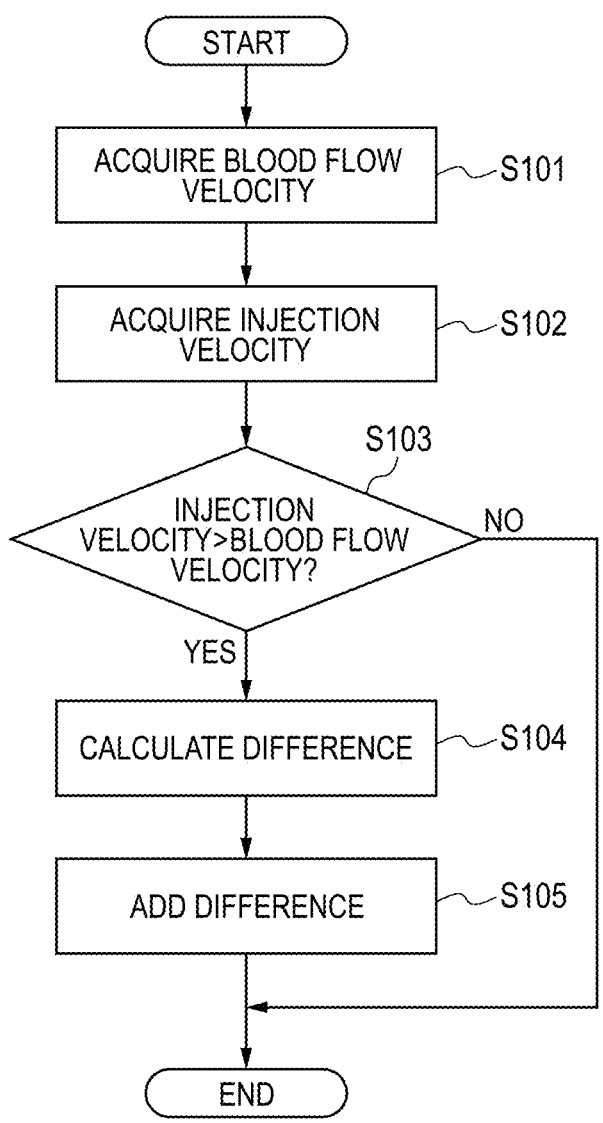
FIG. 10 is a flow chart for illustrating addition processing.

Therefore, the prediction unit 16 predicts the change with time of the pixel value based on the blood flow velocity obtained by the addition. In other words, in predicting the change with time of the pixel value using the above-mentioned mathematical expressions, the prediction unit 16 adds the obtained difference to a blood flow velocity Q per unit tissue volume in the compartment. Specifically, as illustrated in a flow chart of addition processing of FIG. 10, the prediction unit 16 acquires, as the object information, from the object information acquisition unit 11, the normal blood flow velocity of a tissue corresponding to the injection position, that is, a tissue into which the chemical liquid is injected (S101). In addition, the prediction unit 16 acquires the injection velocity of the chemical liquid, which is contained in the injection protocol received from the protocol acquisition unit 12 (S102). The prediction unit 16 may acquire the blood flow velocity after the injection velocity. Alternatively, instead of acquiring from the object information acquisition unit 11, the prediction unit 16 may acquire the blood flow velocity through calculation based on the body weight of the subject to be inspected.

Next, the prediction unit 16 compares the blood flow velocity and the injection velocity to determine whether or not the injection velocity is higher than the blood flow velocity (S103). When the injection velocity is equal to or less than the blood flow velocity (NO in S103), the prediction unit 16 ends the processing without addition. In contrast, when the injection velocity is higher than the blood flow velocity (YES in S103), the prediction unit 16 calculates a difference by subtracting the blood flow velocity of the tissue corresponding to the injection position from the injection velocity (S104). Then, the prediction unit 16 adds the calculated difference to the blood flow velocity (S105), and ends the processing. For example, when the injection velocity is 2.0 mL/sec, and when the blood flow velocity is 1.5 mL/sec, the prediction unit 16 adds 0.5 mL/sec to the blood flow velocity as described below. Then, 2.0 mL/sec is applied as the blood flow velocity after the increase in velocity.

1.5 mL/sec+(injection velocity 2.0 mL/sec−1.5 mL/sec)=2.0 mL/sec

Here, the injection velocity is an injection amount of the chemical liquid per unit time. Therefore, when the contrast medium and the physiological saline are injected simultaneously, the prediction unit 16 performs the addition based on a total injection speed of the contrast medium and the physiological saline. Moreover, when the injection is pushed with the physiological saline at a velocity that is higher than the normal blood flow velocity, the prediction unit 16 performs the addition based on the injection velocity of the physiological saline. After the addition processing is finished, the prediction unit 16 predicts based on the information on the object, which contains the blood flow velocity obtained by the addition, the injection protocol, and the information on the tissue, the change with time of the pixel value for each of the plurality of compartments obtained by dividing the tissue along the blood flow direction. As a result, the blood flow velocity may be more approximated to the actual velocity to improve prediction accuracy of the pixel value.

Figure 11:
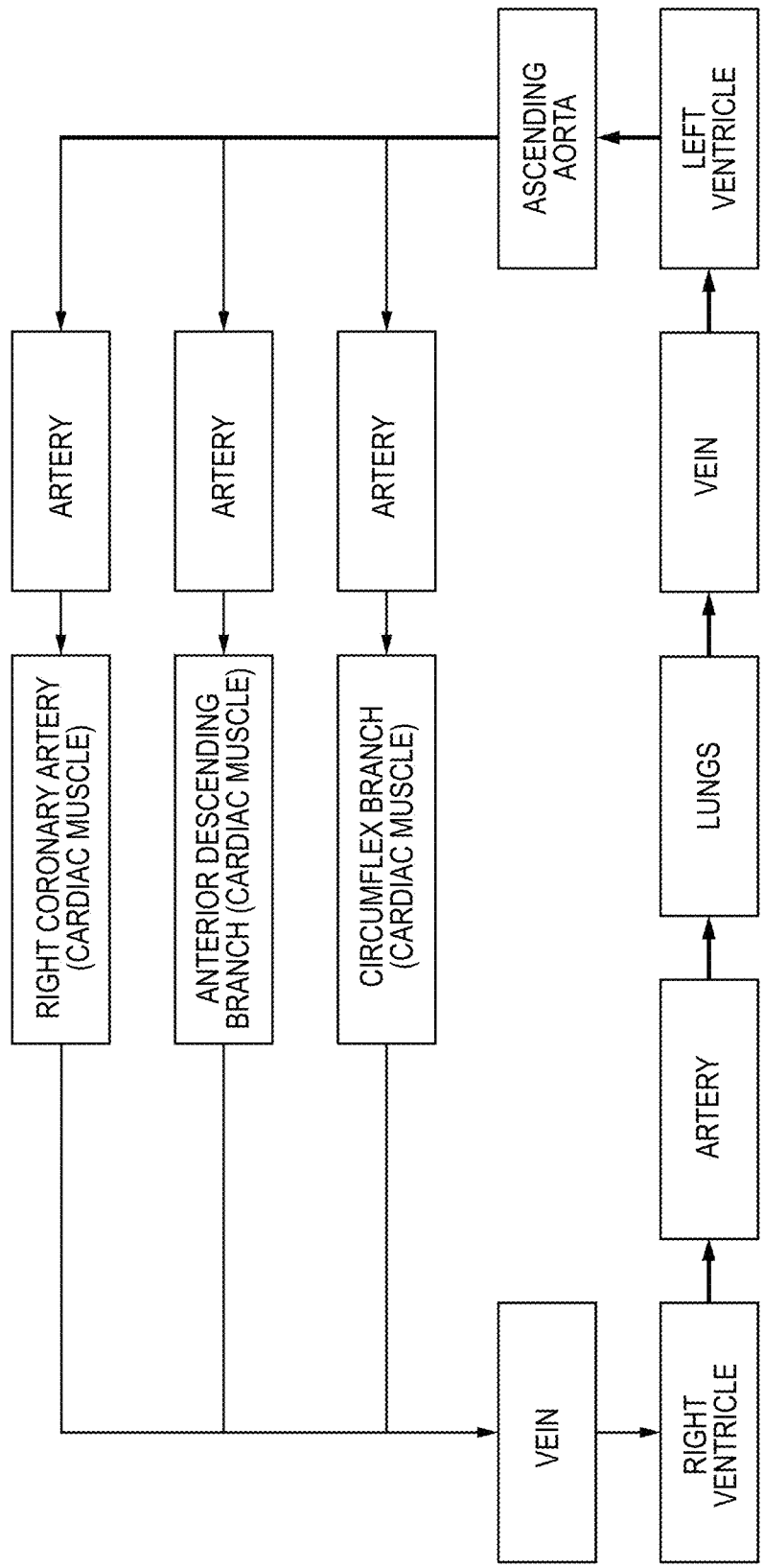
FIG. 11 is a diagram for illustrating a blood flow model according to a modified embodiment of the present invention.

Moreover, in the addition processing, the prediction unit 16 may add the difference to the blood flow velocity with all of the plurality of tissues being addition targets. However, the prediction unit 16 may set some of the plurality of tissues as the addition targets. Specifically, the difference may be added to the blood flow velocity for only tissues extending from a tissue immediately downstream from the tissue corresponding to the injection position in the blood flow direction to the tissue corresponding to the injection position in the blood flow direction. For example, referring to FIG. 11, there is described an example in which the difference is added to the blood flow velocity for only some of the plurality of tissues when the chemical liquid is injected from the upper extremity vein. In FIG. 11, the right ventricle, artery, lungs, vein, left ventricle, ascending aorta, artery, cardiac muscles (cardiac muscle in which the right coronary artery is dominant, cardiac muscle in which the anterior descending branch is dominant, and cardiac muscle in which the circumflex branch is dominant), and vein form a closed circuit with the right ventricle being a starting point. In other words, those tissues form the closed circuit for the tissue corresponding to the injection position with the right ventricle, which is located immediately downstream in the blood flow direction, being the starting point. Therefore, the prediction unit 16 sets, as the addition targets, only the tissues from the right ventricle to the vein included in the closed circuit, for example, and does not add the difference to the blood flow velocities of the tissues in the lower extremities. As a result, the effect of the addition may be kept within the closed circuit, and hence the simulation may be simplified to reduce calculation time.

Moreover, the prediction unit 16 predicts the changes with time of the pixel values by adding the difference to the blood flow velocities of all the tissues as the addition targets simultaneously with the start of injection of the chemical liquid. However, the prediction unit 16 may predict the changes with time of the pixel values assuming that the difference is added to the blood flow velocities at a time point when a predetermined period of time has elapsed from the start of injection. In other words, in the tissues located downstream from the tissue corresponding to the injection position, the blood flow velocities may change after the predetermined period of time has elapsed from the start of injection in some cases. Therefore, for the tissue corresponding to the injection position, the prediction unit 16 predicts the change with time of the pixel value assuming that the difference is added to the blood flow velocity simultaneously with the start of injection of the chemical liquid. Meanwhile, for a tissue located at a far distance from the tissue in the blood flow direction, the prediction unit 16 predicts a change with time of a pixel value assuming that the difference is added at a time point when time that becomes longer depending on the distance has elapsed.

FIG. 12 is a graph for showing time-density curves, which are prediction results obtained by performing addition processing according to a modified embodiment of the present invention. In FIG. 12, time-density curves for the hepatic artery are shown, in which the horizontal axis corresponds to the elapsed time from the start of injection, and the vertical axis corresponds to the pixel value. Moreover, the height of the subject to be inspected is set to 170 cm, the body weight of the subject to be inspected is set to 70 kg, and the contrast medium density is set to 300 mgI/mL. Moreover, in FIG. 12, there are shown time-density curves in a case where 100 mL of the contrast medium is injected at an injection velocity of 2.0 mL/sec for 50 seconds, and subsequently, 30 mL of the physiological saline is injected for pushing at an injection velocity of 2.0 mL/sec for 15 seconds. A time-density curve in a case where the addition processing is performed is indicated by the solid line, and a time-density curve in a case where the addition processing is not performed is indicated by the broken line.

When the addition processing is not performed, the time when the contrast medium reaches the tissue is delayed. Therefore, as compared to the case where the addition processing is performed, the contrast medium is simulated to arrive at a delayed timing. Therefore, in the time-density curve indicated by the broken line, as indicated by the arrow A of FIG. 12, the second peak of the pixel value is generated. In contrast, when the addition processing is performed, the circulation of the contrast medium is simulated. Therefore, as shown by the time-density curve indicated by the solid line, the second peak is not generated.

Therefore, through the addition processing, the pixel value that is closer to reality can be predicted. Further, the injection for pushing with the physiological saline can also be simulated. Specifically, with the injection for pushing, the contrast medium that is congested after the completion of the injection of the contrast medium is pushed out at an earlier timing. In the time-density curve indicated by the solid line of FIG. 12, as a result of simulating the injection for pushing, the prediction accuracy of the pixel value at the peak is improved so that the pixel value becomes higher.

Further, the prediction unit 16 may consider diffusion of the contrast medium between adjacent compartments. In other words, when there is a difference in density of the contrast medium between the adjacent compartments, the diffusion of the contrast medium occurs from a compartment having a high density to a compartment having a low density. Therefore, the prediction unit 16 may make the prediction of the pixel values so that the contrast medium density of the compartment having the high density is reduced and the contrast medium density of the compartment having the low density is increased, to thereby consider the diffusion of the contrast medium.

Here, when the difference in density is large, the prediction unit 16 sets the reduction amount and the increase amount of the contrast medium density large. Moreover, the prediction unit 16 acquires an osmotic pressure of the contrast medium from the chemical liquid information acquisition unit 14, and when the osmotic pressure is large, sets the reduction amount and the increase amount of the contrast medium density large. Further, when a contact area between the compartments is large, the prediction unit 16 sets the reduction amount and the increase amount of the contrast medium density large. For example, when compartments of different tissues are adjacent to each other, the contact area is small, and hence the prediction unit 16 sets the reduction amount and the increase amount of the contrast medium density small. When compartments of the same tissue are adjacent to each other, the contact area is large, and hence the prediction unit 16 sets the reduction amount and the increase amount of the contrast medium density large.

The prediction unit 16 may calculate the contact area, and when the calculated contact area is large, set the reduction amount and the increase amount of the contrast medium density large. Moreover, the modified embodiment described above may be combined with another embodiment or modified embodiment as appropriate without departing from the present invention.

This application claims the benefit of priority from Japanese Patent Application No. 2014-240006, filed on Nov. 27, 2014, the content of which is incorporated herein by reference.

REFERENCE SIGNS LIST

2: injection device, 3: imaging apparatus, 20: simulator, 11: object information acquisition unit, 12: protocol acquisition unit, 13: tissue information acquisition unit, 15: display control unit, 16: prediction unit, 21: injection head, 26: display unit, 100: imaging system, D: blood flow direction

The invention claimed is:

1. A simulator, which is configured to predict a change with time of a pixel value in a tissue of an object, comprising:
   an object information acquisition unit configured to acquire information on the object;
   a protocol acquisition unit configured to acquire an injection protocol for a contrast medium;
   a tissue information acquisition unit configured to acquire information on the tissue; and
   a prediction unit configured to predict, based on the information on the object, the injection protocol, and the information on the tissue, a change with time of a pixel value of each of a plurality of compartments obtained by dividing the tissue along a blood flow direction, the prediction unit predicting the pixel value of a time point when a predetermined time elapses from a time point of a start of injection.

2. A simulator according to claim 1, wherein the information on the tissue includes a number of compartments in the tissue.

3. A simulator according to claim 1, wherein the information on the tissue includes a seep-out rate and a seep-back rate of the contrast medium in the tissue.

4. A simulator according to claim 1, further comprising:
   a display unit configured to display each of the compartments in a color having a density corresponding to the pixel value; and
   a display control unit configured to control the display unit, wherein
   the display control unit is configured to change light and shade of each of the compartments in accordance with the change with time of the pixel value.

5. A simulator according to claim 4, further comprising
   a storage unit configured to store a result of prediction by the prediction unit, wherein
   the display control unit is configured to change the light and shade of each of the compartments by reading the pixel value of each of the compartments at a predetermined time from the storage unit.

6. A simulator according to claim 5, wherein the display control unit is configured to acquire delay time caused by helical scan, and to read the pixel value at a time obtained by adding the delay time to the predetermined time.

7. A simulator according to claim 1, wherein
   the tissue includes a stomach, a spleen, a pancreas, and an intestinal tract, and
   wherein the prediction unit is configured to predict the change with time of the pixel value while treating the stomach, the spleen, the pancreas, and the intestinal tract as different tissues.

8. A simulator according to claim 1, wherein
   the tissue includes a right ventricle, and
   wherein the prediction unit is configured to predict the change with time of the pixel value of each tissue in order of each of upstream and downstream from the right ventricle in the blood flow direction.

9. A simulator according to claim 1, wherein
   the prediction unit is configured to predict the change with time of the pixel value of each tissue in order of each of upstream and downstream from a tissue on a side of an injection position of the contrast medium in the blood flow direction.

10. A simulator according to claim 1, wherein
    the prediction unit is configured to predict the change with time of the pixel value of each of a plurality of compartments obtained by dividing a first tissue, and to predict the change with time of the pixel value of each of a plurality of compartments obtained by dividing a second tissue, which has a volume larger than that of the first tissue, by a number larger than that of the first tissue.

11. A simulator according to claim 1, wherein,
    when an injection velocity of a chemical liquid is higher than a blood flow velocity, the prediction unit adds a difference, which is obtained by subtracting the blood flow velocity from the injection velocity, to the blood flow velocity to predict the change with time of the pixel value.

12. A simulator according to claim 1, wherein,
    when densities of the contrast medium are different between adjacent compartments of the plurality of compartments, the prediction unit reduces a density in a compartment having a higher density of the contrast medium and increases a density in a compartment having a lower density of the contrast medium to predict the change with time of the pixel value.

13. An injection device, comprising:
    an injection head configured to inject a contrast medium in accordance with an injection protocol; and
    the simulator of claim 1.

14. An imaging system, comprising:
    a medical imaging apparatus configured to take an image of an object; and
    the simulator of claim 1.

15. A non-transitory computer readable medium storing a simulation program for causing a computer to predict a change with time of a pixel value in a tissue of an object, the simulation program causing the computer to function as:
    an object information acquisition unit configured to acquire information on the object;
    a protocol acquisition unit configured to acquire an injection protocol for a contrast medium;
    a tissue information acquisition unit configured to acquire information on the tissue; and
    a prediction unit configured to predict, based on the information on the object, the injection protocol, and the information on the tissue, a change with time of a pixel value of each of a plurality of compartments obtained by dividing the tissue along a blood flow direction, the prediction unit predicting the pixel value of a time point when a predetermined time elapses from a time point of a start of injection.

* * * * *